United States Patent [19]
Ratti et al.

[11] Patent Number: 5,003,064

[45] Date of Patent: Mar. 26, 1991

[54] METHOD FOR THE PREPARATION OF MONOHYDRATE

[75] Inventors: Luigi Ratti, Bergamo; Leone Dall'Asta, Pavia, both of Italy

[73] Assignee: Biochimica Opos SpA, Milan, Italy

[21] Appl. No.: 314,026

[22] Filed: Feb. 23, 1989

[30] Foreign Application Priority Data

Feb. 24, 1988 [IT] Italy ................ 19512 A/88

[51] Int. Cl.$^5$ ........................................ C07D 501/04
[52] U.S. Cl. ................................................ 540/230
[58] Field of Search ...................... 540/230, 228, 219

[56] References Cited

U.S. PATENT DOCUMENTS 3,489,752  1/1970  Crast ............................... 260/243
4,504,657  3/1985  Buzard et al. ........................ 540/230

FOREIGN PATENT DOCUMENTS 1240687  7/1971  United Kingdom .

*Primary Examiner*—Nicholas S. Rizzo
*Attorney, Agent, or Firm*—Armstrong, Nikaido, Marmelstein, Kubovcik & Murray

[57] ABSTRACT

Cefadroxil monohydrate is prepared by solubilizing 7-[D-(−)-α-benzyloxycarbonylamino-α-(p-hydroxyphenyl)acetamido]-3-methyl-3-cephem-4-carboxylic acid by silylation or by salification in an organic solvent, subjecting the solubilized acid in the solvent to catalytic hydrogenation, separating the catalyst from the solution, and adding water to the solution at a pH of about 4 to precipitate cefadroxil monohydrate.

9 Claims, No Drawings

METHOD FOR THE PREPARATION OF MONOHYDRATE

BACKGROUND OF THE INVENTION

The present invention relates to a process for the preparation of 7-[D(-)-α-amino-α-(p-hydroxyphenyl-)acetamido]-3-methyl-3-cephem-4-carboxylic acid monohydrate.

7-[D(-)-α-amino-α-(p-hydroxyphenyl)acetamido]-3-methyl-3-cephem-4-carboxylic acid is an orally active semisynthetic cephalosporin known by its international non-proprietary name (INN) as "cefadroxil". Belgian patent No. 853,974 discloses the monohydrate of 7-[D(-)-α-amino-α-(p-hydroxyphenyl)acetamido]-3-methyl-3-cephem-4-carboxylic acid, hereinafter designated "cefadroxil monohydrate", having the formula:

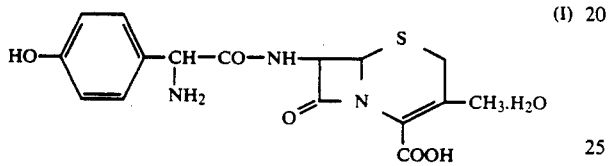

(I)

Cefadroxil monohydrate has the advantage of being a stable form of cefadroxil particularly useful in pharmaceutical formulations.

According to the Belgian patent, cefadroxil monohydrate is prepared by a process comprising:

(a) silylating 7-amino-3-desacetoxycephalosporanic acid in a substantially anhydrous aprotic solvent;

(b) acylating the thus obtained silylated 7-amino-3-desacetotoxycephalosporanic acid with D(-)-α-amino-α-(p-hydroxyphenyl)acetylchloride hydrochloride in a substantially anhydrous aprotic solvent in the presence of an acid acceptor;

(c) removing the silyl radicals by hydrolysis or alcoholysis of the acylation product of step (b); and (d) forming the desired monohydrate I either by bringing the solution pH to a higher value and forming a solvate with dimethylformamide, from which cefadroxil monohydrate is thereafter isolated; or (2) or by raising the pH of the solution and isolating the product by treatment with water.

BRIEF SUMMARY OF THE INVENTION

It has been now found that it is possible to obtain cefadroxil monohydrate directly, without preparing an intermediate solvate and by lowering rather than raising the pH of the solution, by hydrogenolysis of solubilized 7-[D(-)-α-benzyloxycarbonylamino-α-(p-hydroxyphenyl)acetamido]-3-methyl-3-cephem-4-carboxylic acid (the acid is disclosed in U.S. Pat. No. 3,489,752). And, after removal of the hydrogenolysis catalyst, the monohydrate is isolated by precipitation with water, optionally acidified. It has been further found that, by this method, the cefadroxil monohydrate is obtained in excellent yields without need of special purification operations.

Thus, the present invention relates to a process for the preparation of cefadroxil monohydrate of formula I, characterized in that:

(a) 7-[D(-)-α-benzyloxycarbonylamino-α-(p-hydroxyphenyl)acetamido]-3-methyl-3-cephem-4-carboxylic acid of the formula:

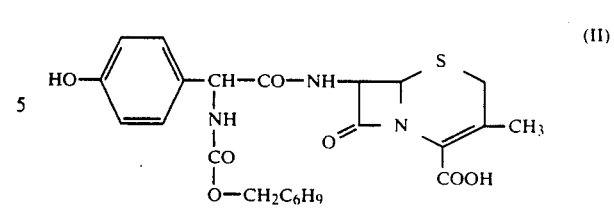

(II)

is solubilized in an organic solvent, in which no solvates are formed with cefadroxil, through silylation or salification with an organic base;

(b) the thus obtained solution is subjected to catalytic hydrogenolysis; and, after removal of the catalyst, (c) the cefadroxil monohydrate is isolated through precipitation with water at a pH of about 4, and filtration.

DETAILED DESCRIPTION OF THE INVENTION

The solubilization of compound II, in step (a), can be carried out by silylation at a temperature from 10° C. to 50° C., preferably at 30° C. to 35° C., for a time period of from 10 minutes to 4 hours, preferably for about one hour. Particularly suitable silylating agents are monotrimethylsilylacetamide (MSA), bis-trimethylsilylacetamide (BSA), bis-trimethylsilylurea (BSU) and hexamethyldisilazane (HMDS). The silylating agent is used in an excess up to about 15% with respect to the calculated amount.

The solubilization of the compound II in step (a) can also be carried out by salification with an organic base, for example trimethylamine or triethylamine.

The solvent used can be either polar or non-polar and is preferably water miscible. Suitable solvents are, for example, dimethoxyethane, isobutyl methyl ketone and acetone, but the preferred solvent is dioxane. Generally any organic solvent can be used, provided that it does not form solvates with cefadroxil, as occurs with methanol and dimethylformamide.

The hydrogenolysis of step (b) is carried out, preferably at room pressure, on the clear solution obtained in step (a) with hydrogen in the presence of a hydrogenation catalyst, preferably palladium on a suitable substrate, more preferably on calcium carbonate, at a concentration of 5 to 10%, preferably 10%.

According to a preferred embodiment, the hydrogenolysis can be carried out using cyclohexene or cyclohexadiene as a hydrogen donor, in the presence of a catalyst, preferably palladium on a suitable substrate, more preferably on carbon at a concentration of 5 to 10%, preferably 5%. Generally, after 2 to 4 hours the hydrogenolysis is complete.

After removal of the catalyst by simple filtration, the cefadroxil monohydrate is isolated in step (c), by adding water to the reaction mixture and filtering the thus obtained precipitate.

When the solubilization of compound II is carried out in step (a) through silylation, step (c) takes place simply by adding water as indicated above, since the pH of the solution at the end of hydrogenolysis is about 4, near the isoelectric point of cefaroxil monohydrate.

When the solubilization of compound II is carried out in step (a) by salification, it is advisable to lower the pH of the solution obtained at the end of the hydrogenolysis from about 7 to 4. In the latter case, the clear solution coming from the hydrogenolysis of step (b) is added to a suitable solvent, preferably acetone. Water made acidic with hydrogen chloride is simultaneously added, for example in the ratio 10:1, so as to maintain the pH at about 4. The operation is preferably carried out at a temperature of from 10° C. to 15° C. Such a process is particularly adapted for the industrial use.

The following examples illustrate the invention without, however, limiting it.

PREPARATIVE EXAMPLE

To a suspension of 0.075 moles of 7-amino-3-desacetoxycephalosporanic acid in 80 ml of methylene chloride, 0.225 mole of hexamethyldisilazane are added. After heating at reflux for 5 hours, the reaction mixture is cooled to −20° C. and then 0.15 mole of N,N-dimethylaniline and subsequently 0.1 mole of the chloride of D(-)-α-benzyloxycarbonylamino-α-(p-hydroxyphenyl)acetic acid are added. The mixture is stirred for 2 hours at from −20° C. to −25° C, and then the temperature is brought to +20° C. over about 2 hours and is maintained for a further 2 hours at the same temperature.

The reaction mixture is then treated with 40 ml of water, the organic phase is separated and extracted with 8% (w/v) aqueous solution of sodium bicabonate. From the aqueous phase, through acidification with hydrogen chloride diluted to pH 3, a crystalline product is obtained, which is filtered, washed with water and dried at 35° C. under reduced pressure. 7-[D(-)-α-benzyloxycarboylamino-α-(hydroxyphenyl)acetamido]-3-methyl-3-cephem-4-carboxylic acid is thus obtained in a yield of 86% of the theoretical; m.p. 118°-121° C. (dec.) Its IR (in KBr) and $^1$H-NMR (in DMSO-d$_6$) spectra are in agreement with the structure for the compound.

EXAMPLE 1

(a) To a suspension of 0.028 mole of the compound obtained in the preparative example in 55 ml of dioxane, 0.070 mole of bis-trimethylsilylacetamide is added. After 15 minutes stirring at 50° C. a clear solution is obtained.

(b) To the thus obtained solution, 0.8 g of 10% palladium on calcium carbonate is added, and the mixture is hydrogenated at 35°–40° C. and 3.5 bar for 3 hours. When hydrogen absorption is completed, the catalyst is filtered off.

(c) To the clear solution, there is added 24 ml of water, and the solution is kept at 5° C. for 15 hours. The resultant crystalline product is filtered, washed with 35 ml of cool water and lastly with acetone. After drying at 30° C. under reduced pressure, a yield of 89% is obtained of cefadroxil monohydrate identical to an authentic sample.

EXAMPLE 2

(a) To a solution of 0.03 mole of the compound obtained in the preparative example in 80 ml of methyl isobutyl ketone, 0.033 mole of triethylamine is added with stirring.

(b) To the thus obtained clear solution, 0.2 of g 10% palladium on calcium carbonate is added, and the mixture is hydrogenated at room temperature and pressure. After 2 hours, the absorption of hydrogen is completed, and the catalyst is filtered off.

(c) The clear solution is added dropwise, over one hour at 10° to 15° C. to 235 ml of acetone, the acetone solution being simultaneously added with water containing 10% of hydrogen chloride, keeping the pH value of the water-acetone solution at about 4. The mixture is stirred for 2 hours, the pH being adjusted to 4, if necessary, by adding hydrogen chloride (1:10). The crystalline product is collected, washed with acetone and dried at 30° C. under reduced pressure. Cefadroxil monohydrate is thus obtained in a 90% yield of the theoretical value.

EXAMPLE 3

(a) To a suspension of 0.028 mole of the product obtained in the preparative example in 55 ml of dimethoxyethane, 0.070 mole of hexamethyldisilazane is added. After 15 minutes stirring, a clear solution is obtained.

(b) To the thus obtained solution, 80 ml of cyclohexene are added and, with stirring under a stream of nitrogen, 0.9 g of 5% palladium on carbon are added. After stirring for three-hours, the catalyst is removed by filtration.

(c) To the thus obtained clear solution, 30 ml of water are added.

Following the procedure of Example 1(c), cefadroxil monohydrate is obtained in a yield of 92% of the theoretical.

We claim:

1. A process for the preparation of cefadroxil monohydrate consisting essentially of:
(a) solubilizing 7-D(-)-alpha-benzyloxycarbonylamino-alpha-(p-hydroxyphenyl)acetamido-3 methyl-3-cephem-4-carboxylic acid in an organic solvent which does not form solvates with cefadroxil by silylation or by salification with an organic base; (b) subjecting the thus silylated or salified acid in the solution to hydrogenolysis in the presence of a catalyst; (c) separating the catalyst from the solution: (d) adding water to the solution at a pH of about 4 to precipitate cefadroxil monohydrate from the solution; and (e) separating the cefadroxil monohydrate which precipitates from the solution.

2. A process according to claim 1, wherein solubilization in step (a) is effected by silylation with monotrimethylsylilacetamide, bis-trimethylsilylacetamide, bis-trimethylsilylurea or hexamethyldisilazane.

3. A process according to claim 1, wherein solubilization in step (a) is effected by salification with trimethylamine or triethylamine.

4. A process according to any one of claims 1 to 3, wherein the organic solvent is dioxane, dimethoxyethane, acetone or methyl isobutyl ketone.

5. A process according to claim 1, wherein the catalyst in step (b) is palladium on calcium carbonate.

6. A process according to claim 5, wherein the concentration of the palladium in the catalyst is 10%.

7. A process according to claim 1, wherein the catalytic hydrogenolysis in step (b) is effected in the presence of cyclohexene or cyclohexadiene as a hydrogen donor.

8. A process according to claim 7, wherein the catalyst is palladium on carbon.

9. A process according to claim 8, wherein the concentration of the palladium in the catalyst is 5%.

* * * * *

UNITED STATES PATENT AND TRADEMARK OFFICE
CERTIFICATE OF CORRECTION

PATENT NO. : 5,003,064

DATED : March 26, 1991

INVENTOR(S) : RATTI et al

It is certified that error appears in the above-identified patent and that said Letters Patent is hereby corrected as shown below:

On the title page, Item [54], "METHOD FOR THE PREPARATION OF MONOHYDRATE", should read, --METHOD FOR THE PREPARATION OF CEFADROXIL MONOHYDRATE--.

Signed and Sealed this

Twenty-eighth Day of July, 1992

Attest:

DOUGLAS B. COMER

*Attesting Officer*   *Acting Commissioner of Patents and Trademarks*